United States Patent
Ramirez et al.

(10) Patent No.: US 10,585,205 B2
(45) Date of Patent: Mar. 10, 2020

(54) ACTIVE DAMPING FOR MULTI-FREQUENCY NMR LOGGING TOOLS

(71) Applicants: Marc Stephen Ramirez, Missouri City, TX (US); Stanislav W. Forgang, Houston, TX (US)

(72) Inventors: Marc Stephen Ramirez, Missouri City, TX (US); Stanislav W. Forgang, Houston, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 21 days.

(21) Appl. No.: 15/874,428

(22) Filed: Jan. 18, 2018

(65) Prior Publication Data
US 2019/0219726 A1 Jul. 18, 2019

(51) Int. Cl.
G01V 3/32 (2006.01)
G01R 33/36 (2006.01)
G01N 24/08 (2006.01)

(52) U.S. Cl.
CPC .............. *G01V 3/32* (2013.01); *G01N 24/081* (2013.01); *G01R 33/3607* (2013.01); *G01R 33/3621* (2013.01); *G01R 33/3671* (2013.01)

(58) Field of Classification Search
CPC ... G01R 33/3607; G01R 33/3621; G01V 2/32
(Continued)

(56) References Cited

U.S. PATENT DOCUMENTS 2,880,389 A * 3/1959 Ferre .................. G01V 3/24
324/373
4,100,483 A * 7/1978 Thompson ........... G01V 3/30
324/341
(Continued)

FOREIGN PATENT DOCUMENTS

WO 2013148516 A1 10/2013
WO 2017058482 A1 4/2017
WO 2017105468 A1 6/2017

OTHER PUBLICATIONS

International Search Report and the Written Opinion of the International Searching Authority; PCT/US2019/013618; dated May 10, 2019; 10 pages.

*Primary Examiner* — Patrick Assouad
*Assistant Examiner* — Demetrius R Pretlow
(74) *Attorney, Agent, or Firm* — Cantor Colburn LLP (57) ABSTRACT

An apparatus for performing a nuclear magnetic resonance (NMR) experiment in a borehole penetrating the earth includes: a carrier configured to be conveyed through the borehole; an antenna assembly disposed on the carrier and configured to receive an NMR signal; and an active gain circuit having an input coupled to the antenna and configured to apply gain to the received NMR signal and to provide an output signal comprising NMR experiment data. The apparatus also includes a feedback circuit configured to feed the output signal back to the input of the active gain circuit; wherein the signal fed back to the input of the active gain circuit is out of phase with the received NMR signal and the feedback circuit provides an electrical quality factor Q value of an antenna assembly that is less than the electrical quality factor Q value of the antenna assembly without the feedback circuit.

19 Claims, 7 Drawing Sheets

(58) Field of Classification Search
USPC .................................................. 324/300–375
See application file for complete search history.

(56) References Cited

U.S. PATENT DOCUMENTS

| | | | | |
|---|---|---|---|---|
| 4,845,434 A * | 7/1989 | Kuckes | ................. | G01R 33/04 |
| | | | | 324/346 |
| 5,081,419 A * | 1/1992 | Meador | ................... | G01V 3/30 |
| | | | | 324/338 |
| 5,339,037 A * | 8/1994 | Bonner | ................... | G01V 3/20 |
| | | | | 324/366 |
| 5,428,293 A * | 6/1995 | Sinclair | ................... | G01V 3/28 |
| | | | | 324/335 |
| 5,814,988 A * | 9/1998 | Itskovich | ................ | G01V 3/32 |
| | | | | 324/303 |
| 5,977,834 A | 11/1999 | Davis et al. | | |
| 6,064,210 A * | 5/2000 | Sinclair | ................... | G01V 3/20 |
| | | | | 324/338 |
| 6,291,944 B1 | 9/2001 | Hesterman et al. | | |
| 6,359,438 B1 * | 3/2002 | Bittar | ....................... | G01V 3/28 |
| | | | | 324/369 |
| 7,109,714 B2 | 9/2006 | Rudakov et al. | | |
| 7,292,041 B2 | 11/2007 | Alvarez et al. | | |
| 7,301,344 B2 | 11/2007 | McCambridge | | |
| 7,639,016 B2 * | 12/2009 | Forgang | ................... | G01V 3/24 |
| | | | | 324/347 |
| 8,686,724 B2 | 4/2014 | Mitchell et al. | | |
| 8,736,264 B2 | 5/2014 | Walsh et al. | | |
| 8,829,907 B2 * | 9/2014 | Signorelli | ................ | G01V 3/30 |
| | | | | 324/338 |
| 9,429,673 B2 | 8/2016 | Walsh et al. | | |
| 2004/0217763 A1 * | 11/2004 | Moore | ..................... | G01V 3/30 |
| | | | | 324/338 |
| 2006/0033499 A1 | 2/2006 | Flexman et al. | | |
| 2008/0183392 A1 * | 7/2008 | Forgang | ................... | G01V 3/24 |
| | | | | 702/12 |
| 2011/0102023 A1 * | 5/2011 | Forgang | ................... | G01V 3/26 |
| | | | | 327/103 |
| 2013/0234706 A1 * | 9/2013 | Mandal | ................ | G01N 24/081 |
| | | | | 324/303 |
| 2013/0314092 A1 * | 11/2013 | Shumway | ................ | G01V 3/40 |
| | | | | 324/346 |
| 2015/0077102 A1 | 3/2015 | Mandal | | |
| 2015/0253396 A1 | 9/2015 | Derby | | |
| 2016/0077178 A1 | 5/2016 | Song et al. | | |
| 2016/0299249 A1 * | 10/2016 | Ramirez | ................... | G01V 3/32 |
| 2017/0198571 A1 | 7/2017 | Chimakurthy | | |
| 2017/0205528 A1 | 7/2017 | Hooper et al. | | |

\* cited by examiner

ACTIVE DAMPING FOR MULTI-FREQUENCY NMR LOGGING TOOLS

BACKGROUND

Geologic formations may be used for many applications such as hydrocarbon production, geothermal production, and carbon dioxide sequestration. Typically, boreholes are drilled into the formations to access them. Various downhole tools or instruments may be conveyed in the boreholes in order to characterize the formations. Characterization of the formations and the fluids within provides valuable information related to the intended use of the formations so drilling and production resources can be used efficiently.

One type of downhole instrument is a nuclear magnetic resonance (NMR) tool that measures nuclear magnetic properties of formation materials such as fluids within a rock matrix. Multi-frequency NMR tools are beneficial because they offer the potential for depth profiling and are compatible with efficient logging acquisitions since multiple frequency and thus multiple depth NMR experiments can be interleaved in time. Multiple frequency experiments, however, require receiving NMR signals over a wide range of frequencies. Hence, innovations that increase the range of tool operating frequencies while preserving a high signal-to-noise ratio (SNR) over that range of measurements would be well received in the drilling and production industries.

SUMMARY

Disclosed is an apparatus for performing a nuclear magnetic resonance (NMR) experiment in a borehole penetrating the earth. The apparatus includes: a carrier configured to be conveyed through the borehole; an antenna assembly disposed on the carrier and configured to receive an NMR signal; an active gain circuit having an input coupled to the antenna and configured to apply gain to the received NMR signal and to provide an output signal comprising NMR experiment data; and a feedback circuit configured to feed the output signal back to the input of the active gain circuit; wherein the signal fed back to the input of the active gain circuit is out of phase with the received NMR signal and the feedback circuit provides an electrical quality factor Q value of an antenna assembly that is less than the electrical quality factor Q value of the antenna assembly without the feedback circuit.

Also disclosed is a method for performing a nuclear magnetic resonance (NMR) experiment in a borehole penetrating the earth. The method includes: conveying a carrier through the borehole; receiving an NMR signal with an antenna assembly disposed on the carrier; applying gain to the received NMR signal with an active gain circuit having an input coupled to the antenna to provide an output signal comprising NMR experiment data; and applying the output signal as a feedback signal to the input of the active gain circuit using a feedback circuit; wherein the signal fed back to the input of the active gain circuit is out of phase with the received NMR signal and the feedback circuit provides an electrical quality factor Q value of an antenna assembly that is less than the electrical quality factor Q value of the antenna assembly without the feedback circuit.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Disclosed are apparatuses and methods for performing a nuclear magnetic resonance (NMR) experiment that provides for the reception of high-bandwidth NMR signals over a diverse range of operating (Larmor) frequencies without substantially deteriorating the low-noise performance of the instrument and/or suffering from substantial after transmitter-burst ringing penalties. This sensitivity preservation compared to conventional measurement in a narrow frequency band is due to feedback in a preamplifier or gain circuit coupled to an NMR antenna where the feedback signal is approximately 180° out of phase with the antenna signal. This feedback signal broadens or spoils (i.e., reduces) the effective quality factor (Q) of the NMR antenna and preamplifier over the wide range of Larmor frequencies thereby increasing the sensitivity to signals detected over a wider measurement range (i.e. more spatial depth and/or more frequencies) than without the feedback circuit.

Figure 1:
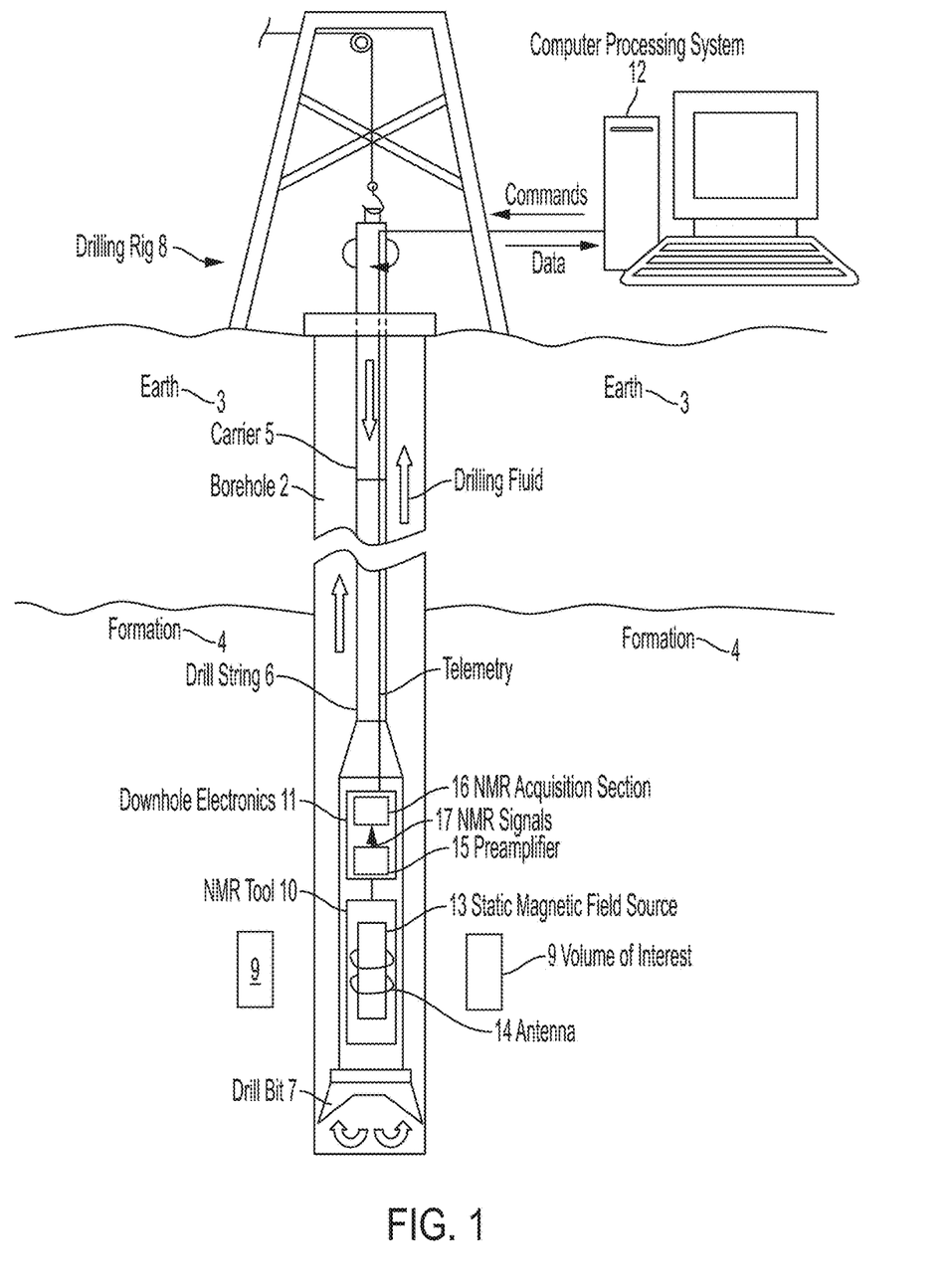
FIG. 1 illustrates a downhole NMR tool disposed in a borehole penetrating the earth.

FIG. 1 illustrates a cross-sectional view of an embodiment of an NMR tool 10 disposed in a borehole 2 penetrating the earth 3, which includes an earth formation 4. The NMR tool 10 is conveyed through the borehole 2 by a carrier 5, which can be a drill tubular such as a drill string 6. A drill bit 7 is disposed at the distal end of the drill string 6. A drill rig 8 is configured to conduct drilling operations such as rotating the drill string 6 and thus the drill bit 7 in order to drill the borehole 2. In addition, the drill rig 8 is configured to pump drilling mud (i.e., drill fluid) through the drill string 6 in order to lubricate the drill bit 7 and flush cuttings from the borehole 2. Downhole electronics 11 are configured to operate the NMR tool 10, process measurement data obtained downhole, and/or act as an interface with telemetry to communicate data or commands between downhole components and a computer processing system 12 disposed at the surface of the earth 3. Non-limiting embodiments of the telemetry include pulsed-mud and wired drill pipe for real time communications. System operation and data processing operations may be performed by the downhole electronics 11, the computer processing system 12, or a combination thereof. In an alternative embodiment, the carrier 5 may be an armored wireline, which can support and convey the NMR tool 10 and also provide a conductor for communications with the surface processing system 12.

The NMR tool 10 is configured to perform multi-frequency NMR measurements on the formation 4. NMR measurements are performed in one or more volumes of interest 9. These volumes may be torus-shaped, surrounding the NMR tool 10, or, when using a side-looking NMR tool, may be directed to one side only. The NMR experiments may measure signals that are a result of the summation of individual spins at various spatial locations within the formation. The measured signals are influenced by a number of factors such as the local field homogeneity, the strength of the static and radiofrequency (RF) magnetic fields, the longitudinal relaxation time constants $T_1$ and/or a transverse relaxation time constants $T_2$ (or distributions thereof, see below), etc. $T_1$ is the time constant describing magnetic polarization of the hydrogen atoms in the volume of interest. $T_2$ represents the exponential decay time constant of spins, which is both a function of the formation fluids and the rock porosity. Transverse relaxation is rapid in high-gradient, multi-frequency NMR requiring data acquisition employing a refocusing scheme (i.e. using a sequence such as CPMG) to account for the strong spin phase incoherence of the hydrogen nuclei (protons) or nuclei of interest within the formation 4 material.

In general, there is not one single value of $T_2$ for fluids contained within formation rock, but a wide distribution of values lying anywhere between fractions of a millisecond (ms) and several seconds for example. The distributions of $T_1$ and $T_2$ values may serve as primary inputs used for fluid typing, allowing the calculation of formation properties, such as porosity, permeability, or fluid properties, such as viscosity and fluid state. These formation properties may be derived as a function of depth into the formation, and together may be referred to as an NMR log. Components in the NMR tool 10 include a static magnetic field source 13 that magnetizes formation fluids and an NMR antenna 14, which may represent one or more antennas, and which transmits precisely timed bursts of radio-frequency energy to excite the spins. In a time period between these pulses, the antenna receives an echo signal from those protons (or nuclei of interest) that are on-resonance with the static magnetic field produced by the magnetic field source. Because a linear relationship exists between the resonance frequency and the strength of the static magnetic field, the frequency of transmitted radio-frequency energy can be tuned to investigate volumes of interest having different diameters or depths around the NMR tool 10. It can be appreciated that the NMR tool 10 may include a variety of components and configurations as known in the art of NMR. In the embodiment of FIG. 1, the downhole electronics 11 include a preamplifier section 15 (also referred to as an active gain section) and an NMR acquisition section 16. The preamplifier section 15 is coupled to the NMR antenna 14 and is configured to amplify an NMR signal received by the NMR antenna 14 and provide received NMR signals 17 to the NMR acquisition section 16. The preamplifier section 15 includes a feedback circuit to provide for wide-band frequency response and is discussed in further detail below. The NMR acquisition section 16 is configured to digitize the received NMR signals 17 to provide useable output that may be processed into NMR logging data. It can be appreciated that the NMR tool 10 may include a variety of components and configurations known in the art of NMR. Consequently, specific details of those NMR components and configurations known in the art are not discussed in further detail.

It can be appreciated that the NMR tool 10 may be calibrated to a known porosity and/or other known properties of a subsurface material by analysis or by testing in field or laboratory conditions using subsurface materials having a known porosity and/or other known properties.

Figure 2:
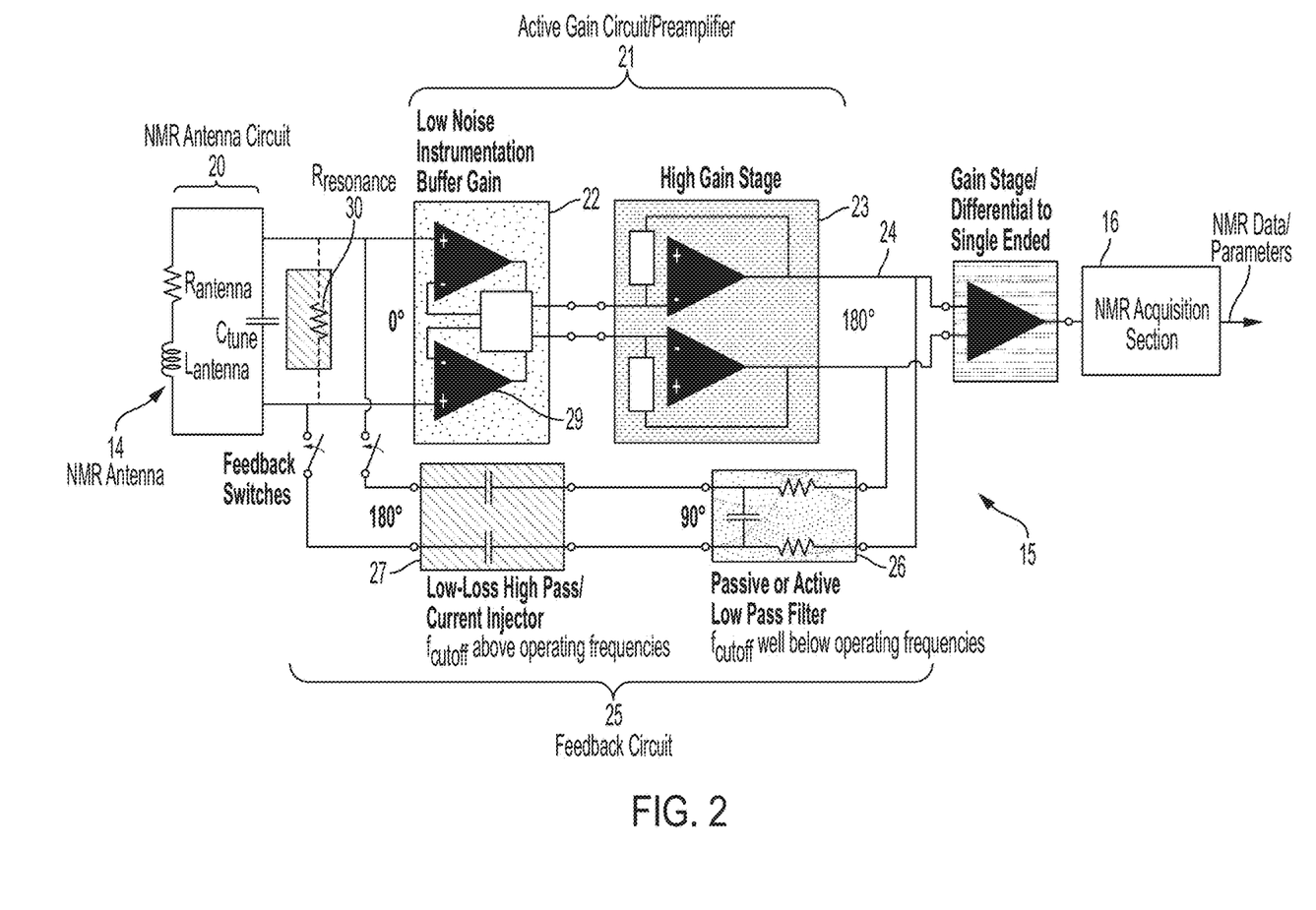
FIG. 2 depicts aspects of an active gain circuit coupled to an NMR antenna in the downhole NMR tool.

FIG. 2 depicts aspects of an active gain circuit (or preamplifier circuit) 21 coupled to the NMR antenna 14 in the downhole NMR tool 10. The NMR antenna 14 is represented by inductance $L_{antenna}$ in series with resistance $R_{antenna}$. A tuning capacitor $C_{tuning}$ is configured to tune the response of the NMR antenna 14 to a specified center frequency. The NMR antenna 14 in combination with the tuning capacitor form an NMR antenna tank circuit 20 (also referred to as an antenna assembly). The output from the NMR antenna tank circuit 20 is coupled to the input of the active gain circuit 21. The active gain circuit 21 includes a low-noise differential instrumentation buffer gain stage 22 that feeds to a high gain stage 23. The buffer gain stage 22 and the high gain stage 23 provide gain to the NMR signal induced in the NMR antenna tank circuit 20 and provide a gain circuit output signal 24 that is out-of-phase (i.e., phase-shifted) with respect to the NMR signal induced in the NMR antenna tank circuit 20. In one or more embodiments, the gain circuit output signal 24 is phase-shifted by 180° or approximately 180° (e.g., +/−20°). In one or more embodiments, the buffer gain stage 21 and the high gain stage 23 use active components such as integral or discrete operational amplifiers 29.

A feedback circuit 25 is provided with the high-gain circuit output signal 24, the feedback circuit 25 modifies this signal according to its transfer function, and feeds the modified signal back to the input of the active gain circuit 21. The feedback circuit 25 includes a low-pass filter 26, which can be a passive or active filter. In one or more embodiments, the low-pass filter 26 is a resistor-capacitor (RC) network as illustrated in FIG. 2. In one or more embodiments, the low-pass filter 26 has a cutoff frequency ($f_{cutoff}$) that is well-below the lowest frequency of operation, providing an approximately (e.g., +/−20°−90° phase-shift and in turn an approximately +90° phase-shift with respect to the output signal from the NMR antenna tank circuit 20. The signal from the low-pass filter 26 is coupled to a high pass filter 27. In one or more embodiments, the high-pass filter 27 has a cutoff frequency ($f_{cutoff}$) that is well above the highest frequency of operation, providing approximately a +90° phase-shift. Hence, a feedback signal 28 has in one or more embodiments a phase-shift that is out of phase (e.g., approximately 180° out of phase) with the signal provided by the NMR antenna circuit 20, thus making the feedback negative and achieving antenna damping or respective Q-spoiling. In one or more embodiments, the high-pass filter 27 is a capacitor network made up of low-loss capacitors as illustrated in FIG. 2 in combination with a resonance resistance $R_{resonance}$ 30. The resonance resistance represents the impedance of the tuned parallel antenna tank circuit at the resonance frequency. Using high quality reactive elements (i.e., capacitors) in combination with low-value non-inductive resistors (resistance being far less than the equivalent active impedance of antenna at the resonance frequency) allows for producing feedback signals 28 that have noise components which are far less than the intrinsic antenna noise.

The result of feeding back an out-of-phase signal to the input of the active gain circuit 21 is that the antenna 20 becomes damped or Q-spoiled without substantially increasing overall noise at the output of gain stage 23 thus allowing to maintain low front-end noise over a wider frequency bandwidth. Achieving a desired level of Q reduction could become an iterative process, where the feedback gain amplitude can be adjusted by a combination of low-pass and high-pass filter responses in the feedback circuit 25.

Still referring to FIG. 2, the gain circuit output signal 24 is provided as input to a differential to single ended gain stage 31. The differential gain stage 31 is coupled to the NMR acquisition section 16 and in some embodiments this coupling could include conversion from differential to a single ended output. The NMR acquisition section 16 is configured to sense and process NMR echoes received by the NMR antenna 14 for further enhanced data processing. In that the NMR acquisition section is known in the art, it is not discussed in further detail.

Figure 3A:
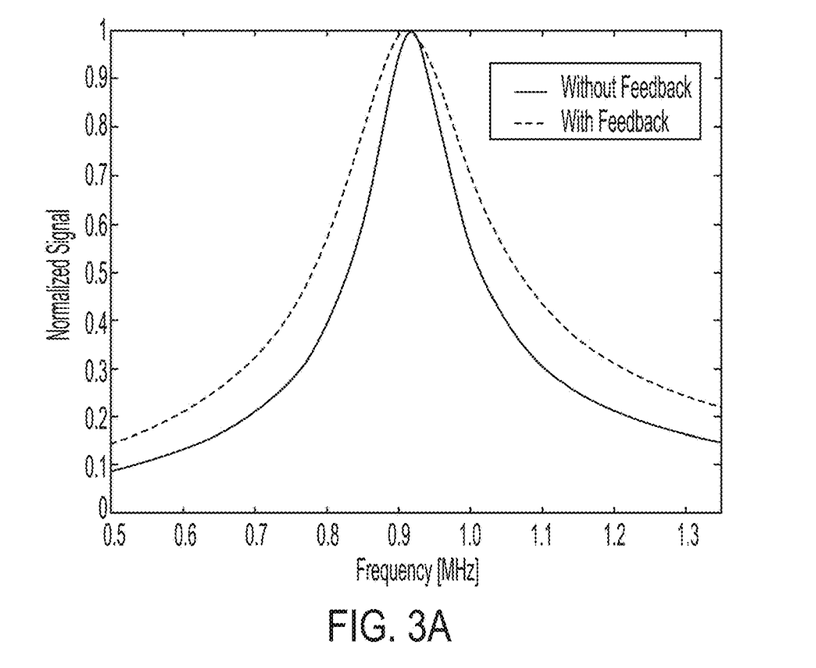
FIGS. 3A and 3B, collectively referred to as FIG. 3, depict aspects of damping or Q-spoiling for an NMR antenna circuit in order to increase the range of operating frequencies while preserving high signal-to-noise ratio.
Figure 3B:
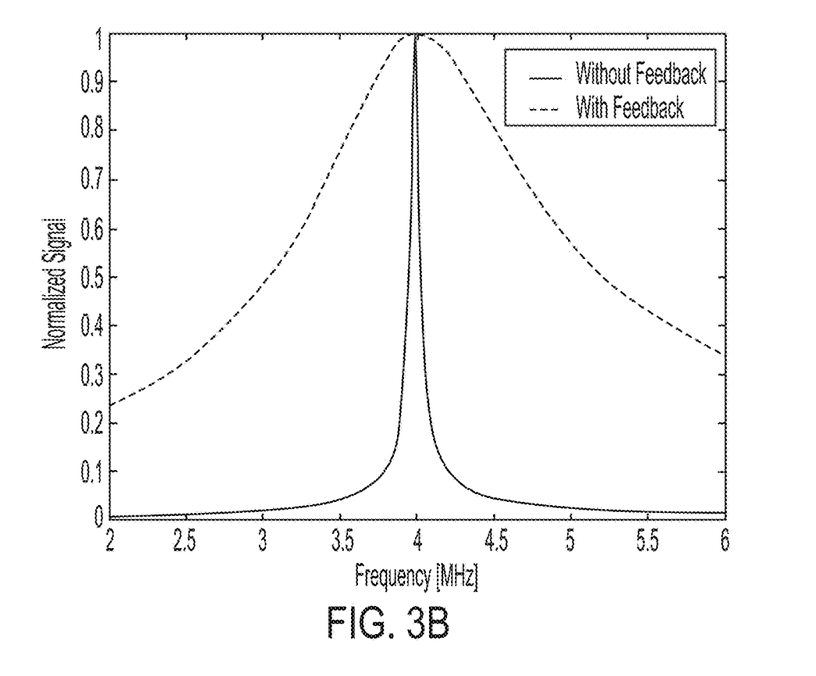

FIG. 3 depicts aspects of damping or Q-spoiling in order to widen the frequency bands of operation. FIG. 3A illustrates the response of the NMR antenna/preamplifier circuit with (dashed line) and without (solid line) feedback over a frequency range of 0.5 to 1.35 MHz. FIG. 3B illustrates the response from the NMR antenna/preamplifier circuit with (dashed line) and without (solid line) feedback over a frequency range of 2 to 6 MHz. It can be seen that the feedback provides the potential for increased receiver bandwidth compared to the narrowband sensitivity without feedback. Furthermore, the same circuit components were used to generate the plots of FIG. 3A and FIG. 3B, indicating the potential for broadband, multi-frequency NMR logging with a robust circuit that does not require switching in various components for the different frequencies of operation. Of note, more Q-spoiling is achieved at higher frequencies than at lower frequencies, which follows the requirement of compensating for a high gradient of static magnetic field strength at shallower radial formation depths and a lower gradient at deeper radial depths, as a result of the decreasing rate of static magnetic field strength decay deeper into the formation.

Figure 4A:
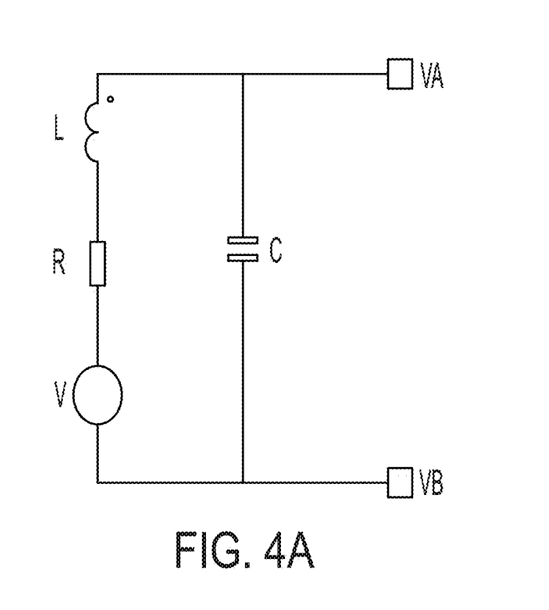
FIGS. 4A and 4B, collectively referred to as FIG. 4, depict aspects of a conventional NMR antenna.

The theory behind the operation of the feedback circuit is now discussed in further detail. Conventional devices are first discussed. A "conventional" NMR antenna tank circuit, as illustrated in FIG. 4A, is generally built as a tuned parallel tank circuit at operating frequency $f_0$ and having an inductive antenna; this antenna is characterized by its intrinsic inductance L and losses R. When an external magnetic field crosses the antenna it induces electro-motive force or e.m.f. in the winding (denoted by V); however, the e.m.f. may be quite low, compromising the reliability of measurements. To increase signal value over the noise (generated by active losses R) the antenna becomes tuned to the operating frequency $f_0$ by external capacitor C. The tuning results in increasing voltage across the antenna $\Delta V = |VA-VB|$ in FIG. 4A which is proportional to the electrical quality factor of the antenna $Q=2 \cdot \pi \cdot f_0 \cdot L/R$ and simultaneously shrinks the response bandwidth around frequency $f_0$. Overall it can be shown that tuning the antenna to the resonance frequency can increase the measurement signal-to-noise ratio (SNR) by $\sqrt{Q}$ times.

Figure 4B:
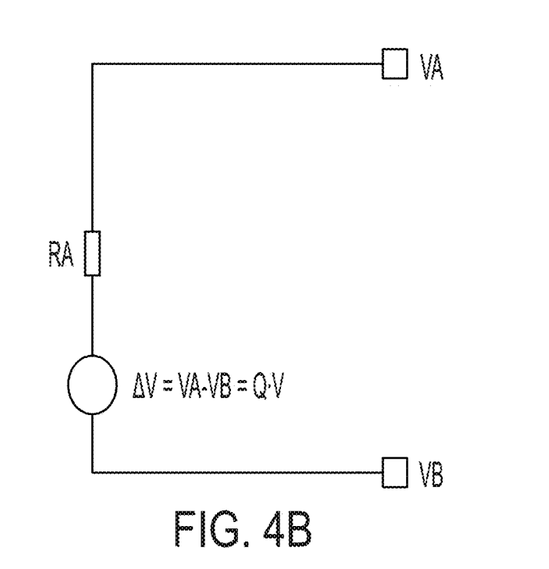

After all transformations, the antenna behavior at resonance can be simplified to the one shown in FIG. 4B where $RA=2 \cdot \pi \cdot f_0 \cdot L \cdot Q$ represents the equivalent characteristic impedance of the antenna at resonance frequency $f_0$ (with only an active part at frequency $f=f_0$. The value of this impedance can be quite significant and depending on the design approach, it could reach tens of hundreds of ohms or more within the tool operating range. In this case a conventionally selected approach of operating at a single frequency would be to measure antenna signal $\Delta V$ with a low noise amplifier that has an input impedance significantly higher than RA. The amplifier should not practically contribute to the overall system noise while providing for a sufficient gain, thus allowing the digital acquisition electronics to operate within its specifications.

However, the case of wide-band operation as described herein for multi-frequency operation, antenna "modification" is required. In particular, it is desired to preserve low antenna noise while decreasing electrical quality Q, i.e., to both widen the antenna bandwidth and reduce transmitter-burst ringing penalties (known in the art as NMR measurement errors). Decreasing antenna Q by increasing internal losses R or shunting the antenna by an external active resistor (needed to reduce energy stored in reactive elements by dissipating will not work properly for at least two reasons. The first reason is that increasing internal active losses will result in increasing Johnson-Nyquist noise while reducing the overall useful signal. In the case of using an external shunt, the external active element (resistor or component acting as a resistor) would not only dissipate part of electromagnetic energy stored in the antenna tank, but also add its own Johnson-Nyquist noise to the total noise value. It can be mathematically demonstrated that the end effect of both approaches could again be represented by the schematics FIG. 4B with a modified RA. There is a consequence of shifting the resonance frequency due to the change in antenna losses, and it typically becomes more pronounced with external shunting.

The general solution as disclosed herein involves applying a negative and substantially "noiseless" feedback signal to the terminals A and B where "noiseless" means that the noise component in the feedback signal is negligible compared to the intrinsic noise of the antenna, and "negative" indicates that the phase of the feedback signal should be opposite (i.e., 180° out of phase) or approximately opposite to the phase of the antenna voltage $\Delta V$. If de-phasing is less than 90° or larger than 270°, the system could become unstable, while within the range of approximately 180° (e.g., +/−20°), the difference in performance is almost negligible.

As follows, the desired signal can be found at the output of the low noise amplifier provided that it has an inverting output (Alternatively, the output of the low noise amplifier could be non-inverting, in which case the feedback circuit would require a total 180 degree or approximately 180 degree phase shift). But, the routing of this signal back to antenna is challenging. As disclosed herein, an optimum solution to the challenge is to bring a feedback signal to the antenna through a small noiseless reactance such as a capacitor as an element that has high external noise immunity. Issues with this might be: relatively lower feedback signal level which could be compensated by increasing the gain of the preamplifier; and unavoidable additional phase shift resulting from using a small capacitor.

Figure 5:
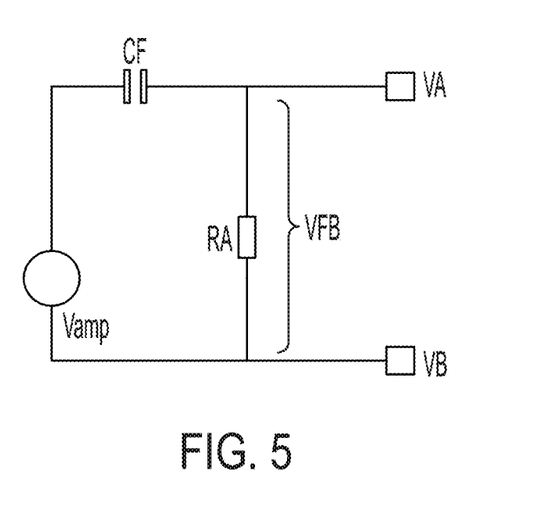
FIG. 5 depicts aspects of a feedback phase shift mechanism while using a small capacitor as a current source.

The reason a small reactance alone will introduce an additional phase shift can be understood with reference to FIG. 5. In FIG. 5, the pre-amplifier output voltage Vamp is applied to the feedback capacitor CF to produce a feedback voltage VFB across the equivalent antenna resistance at resonance RA. (If the antenna were ideal, i.e., R→0 and RA→infinity, and tuned exactly to the resonance frequency $f_0$ then the current in the inductor would be 90° behind VFB, and 90° ahead of VFB in the capacitor. (In FIG. 5, $$VFB = Vamp \frac{RA}{RA + (i \cdot 2 \cdot \pi \cdot f0 \cdot CF)^{-1}}$$

where $i=\sqrt{-1}$, and for $RA << (i \cdot 2 \cdot \pi \cdot f_0 \cdot CF)^{-1}$ the voltage VFB will be almost 90° ahead of Vamp. As discussed previously, this phase shift would not help to maintain desired performance and it needs to be compensated for. This compensation has been provided by a passive or active low pass filter as illustrated in FIG. 2.

The purpose of the low-pass filter is to compensate the undesirable phase shift produced by reactive feedback with a small capacitor. Note that the low-pass filter illustrated in FIG. 2 serves as an example and compensation could be achieved inside the pre-amp itself, preferably in the high gain stage; however, its principle would remain the same. In one or more embodiments, the low-pass filter is a first order RC filter with the following requirements:

(1) The filter's cut-off frequency F should be significantly lower than the lowest operating frequency in the tool's embodiment. In this case the filter's output signal will be always approximately 90° behind of the voltage on its input (Vamp);

(2) the filter's output impedance over the full frequency range is significantly lower than reactance of capacitor CF thus not compromising the performance of this capacitor; and (3) resistors incorporated in the filter should have sufficiently small values to not decrease overall feedback signal-to-noise performance (generally correct with a sufficiently large gain of pre-amplifier, they increase noise by no more than approximately 1%).

The low-pass filter delays the signal by 90° based on the following discussion. For a given filter capacitor C and resistors R, the voltage transfer function "input-output" can be written as $$k = \frac{(i \cdot 2 \cdot \pi \cdot f \cdot C)^{-1}}{2R + (i \cdot 2 \cdot \pi \cdot f \cdot C)^{-1}}.$$

The filter cut-off frequency is when the magnitude of the output signal is $1/\sqrt{2}=0.707$ times the input voltage. This happens when the active part of the filter is equal to its reactive part, i.e., $2R=(i \cdot 2 \cdot \pi \cdot f \cdot C)^{-1}$. For much higher frequencies i.e. when $2R>>(i \cdot 2 \cdot \pi \cdot f \cdot C)^{-1}$, the output voltage gets attenuated even more (and needs to be gained); however, its phase becomes delayed:

$$k \approx \frac{(i \cdot 2 \cdot \pi \cdot f \cdot C)^{-1}}{2R} = \frac{1}{i}\frac{(2 \cdot \pi \cdot f \cdot C)^{-1}}{2R} = \frac{(2 \cdot \pi \cdot f \cdot C)^{-1}}{2R} \cdot e^{-i}$$

Figure 6A:
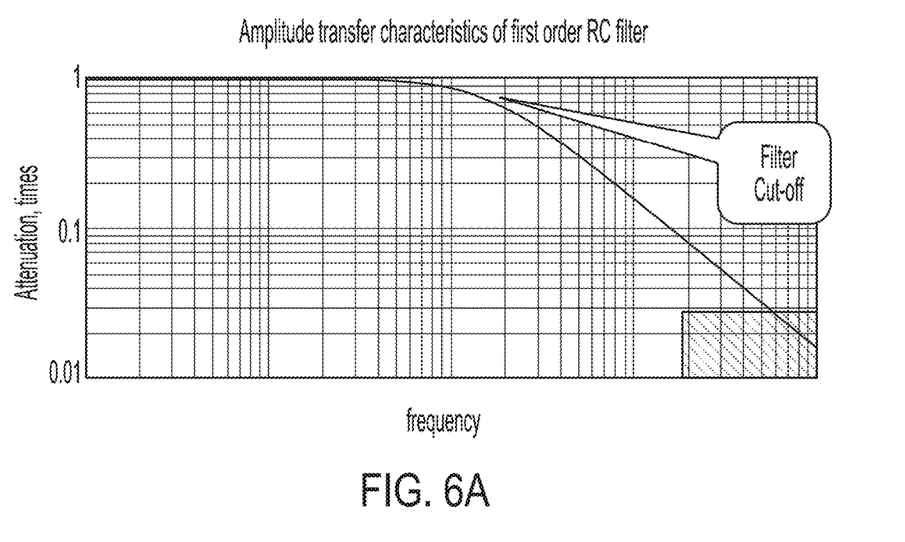
FIGS. 6A and 6B, collectively referred to as FIG. 6, depict characteristics of a first order low-pass RC filter.
Figure 6B:
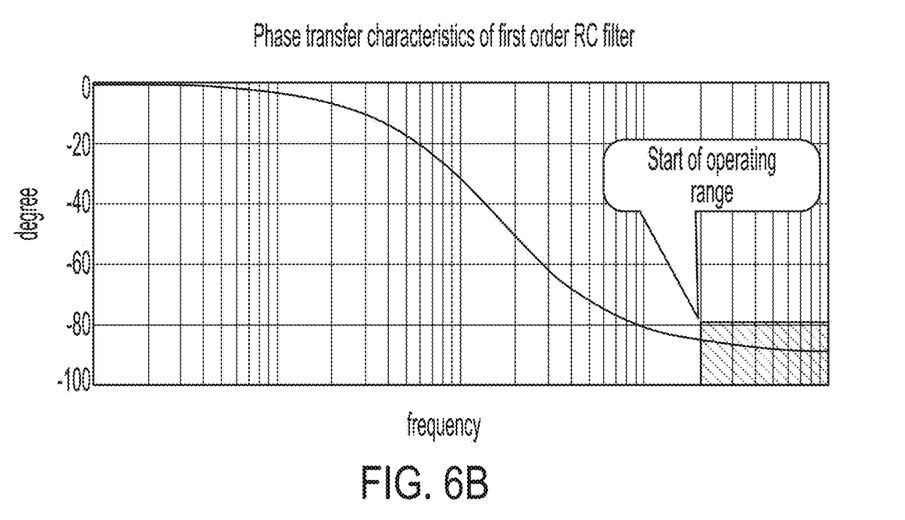

(in conventional electrical engineering abbreviation, Euler's identity $e^{-i}$ stands for a 90 degree phase shift in a monochromatic equation for the output variable provided that the input monochromatic variable has had initial phase of 0 degree). Accordingly, the combination of the small reactance and phase-delayed filter provides for the desired feedback phase. The selection of filter parameters generally depends on the lowest operating frequency. FIG. 6 illustrates one example of transfer characteristics of a first-order low pass RC filter as a function of frequency. FIG. 6A illustrates amplitude transfer characteristics, while FIG. 6B illustrates phase transfer characteristics.

Figure 7:
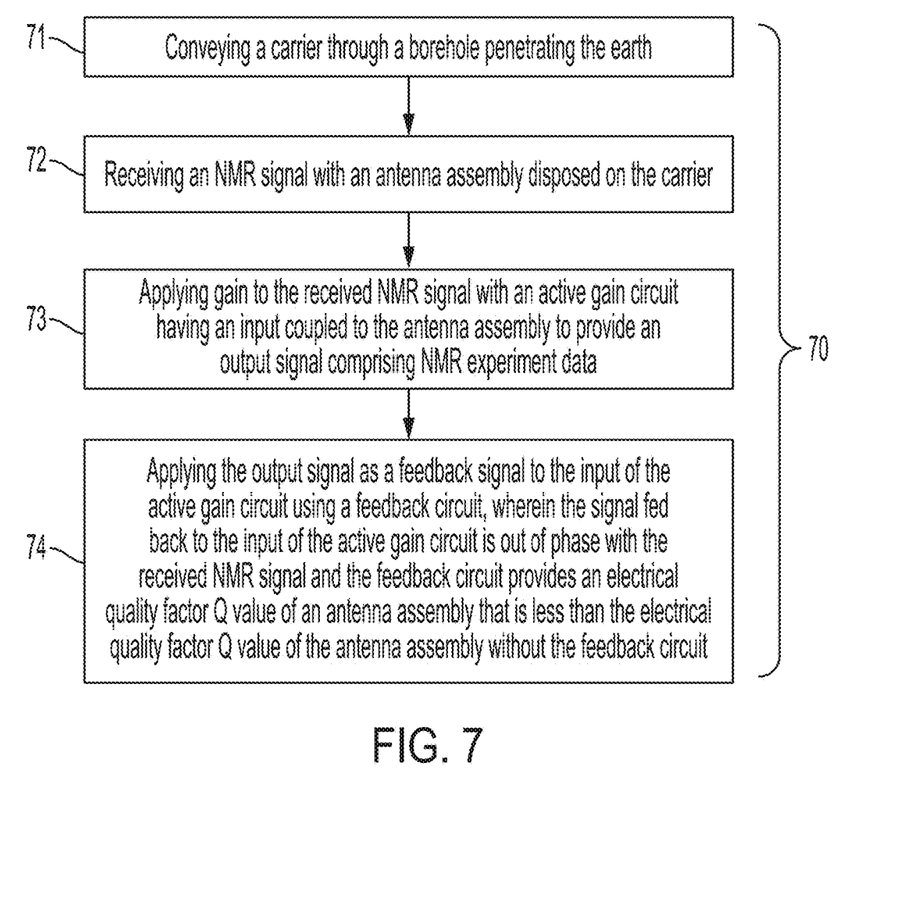
FIG. 7 is a flow chart for a method for performing a downhole NMR experiment.

FIG. 7 is a flow chart for a method 70 for performing a nuclear magnetic resonance (NMR) experiment in a borehole penetrating the earth. Block 71 calls for conveying a carrier through the borehole. Block 72 calls for receiving an NMR signal with an antenna assembly disposed on the carrier. In general, received NMR signals are "echoes" due to nuclei precessing in a magnetic field as a result of transmitted electromagnetic energy stimulating those nuclei. Block 73 calls for applying gain to the received NMR signal with an active gain circuit having an input coupled to the antenna assembly to provide an output signal comprising NMR experiment data. In one or more embodiments, the term "out of phase" relates to the output signal being 180°+/−20° out of phase with the received NMR signal. In one or more embodiments, this block includes phase-shifting the received NMR signal using the active gain circuit such that the output signal is out of phase with the received NMR signal. Block 74 calls for applying the output signal as a feedback signal to the input of the active gain circuit using a feedback circuit, wherein the signal fed back to the input of the active gain circuit is out of phase with the received NMR signal and the feedback circuit provides an electrical quality factor Q value of an antenna assembly that is less than the electrical quality factor Q value of the antenna assembly without the feedback circuit. In one or more embodiments, this block includes phase-shifting the output signal using the feedback circuit such that the signal fed back to the input of the active gain circuit is out of phase with the received NMR signal.

The method 70 may also include filtering the output signal with a low-pass filter in the feedback circuit to provide a low-pass filtered signal. The method 70 may also include phase-shifting the output signal with the low-pass filter to provide a −90° phase-shift. The method 70 may also include filtering the low-pass filtered signal with a high-pass filter in the feedback circuit to provide a high-pass filtered signal. The method 70 may also include phase-shifting the low-pass filtered signal with the high-pass filter to provide an additional +90° phase-shift.

The combination of the active gain amplifier (or preamplifier) and the feedback circuit provides several advantages. One advantage is preserving sensitivity to NMR signals over a wide range of frequencies. Another advantage is the improvement in inherent active damping of any transmit signal induced on the receive coil, allowing the potential for more rapid data acquisition between echoes, i.e. the "echo time" can be reduced.

Using low-loss components in the feedback circuit provides advantages over other types of feedback circuits. One type of feedback circuit involves connecting the preamplifier's output directly to the NMR antenna without additional circuit components. This may not work as conventionally the low output impedance of the preamplifier would produce a "floating" ground potential at the antenna terminal(s) and thus, depending on amplifier architecture, effectively shunting the antenna voltage to almost $\Delta V \approx 0$. Another type of feedback circuit is to place a resistor between the output of the preamplifier and antenna terminals. This would provide for the negative signal; however, it will not be "noiseless" as the resistor value should be sufficiently larger compared to RA and its noise will added to the input signal. Yet another type of feedback circuit is to place a "noiseless" reactance such as high quality capacitor or near-ideal inductance between amplifier output and antenna. The problem with this type of feedback circuit is that to provide for a "negative" feedback voltage the value of these components should be large and as such they will result in shifting the resonance frequency of the NMR antenna (using a small reactance was discussed above in paragraph [0028]).

It can be appreciated that the same circuit components can be used to accommodate both high frequency Q spoiling and low frequency Q spoiling without changing component values. Alternatively, different component values may be switched in the circuitry using switching circuits to optimize the feedback approach for each operating frequency.

Set forth below are some embodiments of the foregoing disclosure:

Embodiment 1

An apparatus for performing a nuclear magnetic resonance (NMR) experiment in a borehole penetrating the earth, the apparatus comprising: a carrier configured to be conveyed through the borehole; an antenna assembly disposed on the carrier and configured to receive an NMR signal; an active gain circuit having an input coupled to the antenna assembly and configured to apply gain to the received NMR signal and to provide an output signal comprising NMR experiment data; and a feedback circuit configured to feed the output signal back to the input of the active gain circuit; wherein the signal fed back to the input of the active gain circuit is out of phase with the received NMR signal and the feedback circuit provides an electrical quality factor Q value of an antenna assembly that is less than the electrical quality factor Q value of the antenna assembly without the feedback circuit.

Embodiment 2

The apparatus according to any prior embodiment, wherein the active gain circuit is configured to provide a phase shift to the received NMR signal such that the output signal is out of phase with the received NMR signal.

Embodiment 3

The apparatus according to claim 1, wherein the feedback circuit is configured to provide a phase shift to the output signal such that the signal fed back to the input of the active gain circuit is out of phase with the received NMR signal.

Embodiment 4

The apparatus according to any prior embodiment, wherein the output signal is at least substantially 180° out of phase with the received NMR signal and within a selected range about a 180° out of phase reference signal.

Embodiment 5

The apparatus according to any prior embodiment, wherein the NMR signal comprises a plurality of NMR signals, each NMR signal in the plurality being in response to transmitted NMR signals having different frequencies.

Embodiment 6

The apparatus according to any prior embodiment, further comprising an NMR acquisition system configured to receive the output signal from the active gain circuit and to process the output signal to provide NMR logging data.

Embodiment 7

The apparatus according to any prior embodiment, wherein the feedback circuit comprises a low-pass filter in series with a high-pass filter, the low-pass filter being configured to receive the output signal, the high-pass filter being configured to provide the feedback signal to the input of the active gain circuit.

Embodiment 8

The apparatus according to any prior embodiment, wherein the low-pass filter comprises a resistance-capacitance network.

Embodiment 9

The apparatus according to any prior embodiment, wherein the low-pass filter is configured to provide an approximately −90° phase-shift of the output signal in a range of operating frequencies.

Embodiment 10

The apparatus according to any prior embodiment, wherein the high-pass filter comprises a capacitance network in combination with impedance of the antenna assembly at resonance.

Embodiment 11

The apparatus according to any prior embodiment, wherein the high-pass filter is configured to provide an approximately +90° phase-shift of a signal output by the low-pass filter.

Embodiment 12

The apparatus according to any prior embodiment, further comprising a transmitter having an antenna, the transmitter being configured to transmit NMR signals at multiple frequencies.

Embodiment 13

A method for performing a nuclear magnetic resonance (NMR) experiment in a borehole penetrating the earth, the method comprising: conveying a carrier through the borehole; receiving an NMR signal with an antenna assembly disposed on the carrier; applying gain to the received NMR signal with an active gain circuit having an input coupled to the antenna assembly to provide an output signal comprising NMR experiment data; and applying the output signal as a feedback signal to the input of the active gain circuit using a feedback circuit; wherein the signal fed back to the input of the active gain circuit is out of phase with the received NMR signal and the feedback circuit provides an electrical quality factor Q value of an antenna assembly that is less than the electrical quality factor Q value of the antenna assembly without the feedback circuit.

Embodiment 14

The method according to any prior embodiment, further comprising phase-shifting the received NMR signal using the active gain circuit such that the output signal is out of phase with the received NMR signal.

Embodiment 15

The method according to any prior embodiment, further comprising phase-shifting the output signal using the feedback circuit such that the signal fed back to the input of the active gain circuit is out of phase with the received NMR signal.

Embodiment 16

The method according to any prior embodiment, further comprising filtering the output signal with a low-pass filter in the feedback circuit to provide a low-pass filtered signal.

Embodiment 17

The method according to any prior embodiment, further comprising phase-shifting the output signal with the low-pass filter to provide an approximately −90° phase-shift in a range of operating frequencies.

Embodiment 18

The method according to any prior embodiment, further comprising filtering the low-pass filtered signal with a high-pass filter in the feedback circuit to provide a high-pass filtered signal.

Embodiment 19

The method according to any prior embodiment, further comprising phase-shifting the low-pass filtered signal with the high-pass filter to provide an approximately +90° phase-shift.

In support of the teachings herein, various analysis components may be used, including a digital and/or an analog system. For example, the downhole electronics 11 and/or the surface computer processing system 15 may include digital and/or analog systems. The system may have components such as a processor, storage media, memory, input, output, communications link (wired, wireless, optical or other), user interfaces (e.g., a display or printer), software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" and the like are intended to be inclusive such that there may be additional elements other than the elements listed. The conjunction "or" when used with a list of at least two terms is intended to mean any term or combination of terms. The term "configured" relates one or more structural limitations of a device that are required for the device to perform the function or operation for which the device is configured.

The flow diagram depicted herein is just an example. There may be many variations to this diagram or the steps (or operations) described therein without departing from the spirit of the invention. For instance, the steps may be performed in a differing order, or steps may be added, deleted or modified. All of these variations are considered a part of the claimed invention.

The disclosure illustratively disclosed herein may be practiced in the absence of any element which is not specifically disclosed herein.

While one or more embodiments have been shown and described, modifications and substitutions may be made thereto without departing from the scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims.

What is claimed is:

1. An apparatus for performing a nuclear magnetic resonance (NMR) experiment in a borehole penetrating the earth, the apparatus comprising:
   a carrier configured to be conveyed through the borehole;
   an antenna assembly disposed on the carrier and configured to receive an NMR signal;
   an active gain circuit having an input coupled to the antenna assembly and configured to apply gain to the received NMR signal and to provide an output signal comprising NMR experiment data; and
   a feedback circuit configured to feed the output signal back to the input of the active gain circuit;
   wherein the signal fed back to the input of the active gain circuit is out of phase with the received NMR signal and the feedback circuit provides an electrical quality factor Q value of an antenna assembly that is less than the electrical quality factor Q value of the antenna assembly without the feedback circuit.

2. The apparatus according to claim 1, wherein the active gain circuit is configured to provide a phase shift to the received NMR signal such that the output signal is out of phase with the received NMR signal.

3. The apparatus according to claim 1, wherein the feedback circuit is configured to provide a phase shift to the output signal such that the signal fed back to the input of the active gain circuit is out of phase with the received NMR signal.

4. The apparatus according to claim 1, wherein the output signal is at least substantially 180° out of phase with the received NMR signal and within a selected range about a 180° out of phase with the received NMR signal.

5. The apparatus according to claim 1, wherein the NMR signal comprises a plurality of NMR signals, each NMR signal in the plurality being in response to transmitted electromagnetic energy having different frequencies.

6. The apparatus according to claim 1, further comprising an NMR acquisition system configured to receive the output signal from the active gain circuit and to process the output signal to provide NMR logging data.

7. The apparatus according to claim 1, wherein the feedback circuit comprises a low-pass filter in series with a high-pass filter, the low-pass filter being configured to receive the output signal, the high-pass filter being configured to provide the signal fed back to the input of the active gain circuit.

8. The apparatus according to claim 7, wherein the low-pass filter comprises a resistance-capacitance network.

9. The apparatus according to claim 8, wherein the low-pass filter is configured to provide an approximately −90° phase-shift of the output signal in a range of operating frequencies.

10. The apparatus according to claim 7, wherein the high-pass filter comprises a capacitance network in combination with impedance of the antenna assembly at resonance.

11. The apparatus according to claim 10, wherein the high-pass filter is configured to provide an approximately +90° phase-shift of a signal output by the low-pass filter.

12. The apparatus according to claim 1, further comprising a transmitter having an antenna, the transmitter being configured to transmit electromagnetic energy at multiple frequencies.

13. A method for performing a nuclear magnetic resonance (NMR) experiment in a borehole penetrating the earth, the method comprising:
conveying a carrier through the borehole;
receiving an NMR signal with an antenna assembly disposed on the carrier;
applying gain to the received NMR signal with an active gain circuit having an input coupled to the antenna assembly to provide an output signal comprising NMR experiment data; and
applying the output signal as a feedback signal to the input of the active gain circuit using a feedback circuit;
wherein the signal fed back to the input of the active gain circuit is out of phase with the received NMR signal and the feedback circuit provides an electrical quality factor Q value of an antenna assembly that is less than the electrical quality factor Q value of the antenna assembly without the feedback circuit.

14. The method according to claim 13, further comprising phase-shifting the received NMR signal using the active gain circuit such that the output signal is out of phase with the received NMR signal.

15. The method according to claim 13, further comprising phase-shifting the output signal using the feedback circuit such that the signal fed back to the input of the active gain circuit is out of phase with the received NMR signal.

16. The method according to claim 13, further comprising filtering the output signal with a low-pass filter in the feedback circuit to provide a low-pass filtered signal.

17. The method according to claim 16, further comprising phase-shifting the output signal with the low-pass filter to provide an approximately −90° phase-shift in a range of operating frequencies.

18. The method according to claim 16, further comprising filtering the low-pass filtered signal with a high-pass filter in the feedback circuit to provide a high-pass filtered signal.

19. The method according to claim 18, further comprising phase-shifting the low-pass filtered signal with the high-pass filter to provide an approximately +90° phase-shift.

* * * * *